United States Patent
Graze, Jr.

(10) Patent No.: US 7,549,350 B2
(45) Date of Patent: Jun. 23, 2009

(54) DILUTION TUNNEL

(75) Inventor: Russell R. Graze, Jr., Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 11/353,034

(22) Filed: Feb. 14, 2006

(65) Prior Publication Data

US 2006/0130599 A1 Jun. 22, 2006

Related U.S. Application Data

(62) Division of application No. 10/151,338, filed on May 20, 2002, now Pat. No. 7,044,009.

(51) Int. Cl.
*G01N 1/20* (2006.01)

(52) U.S. Cl. ............... 73/863.81; 73/863.83; 73/23.31; 73/865.5

(58) Field of Classification Search ............ 73/863, 73/863.83, 863.81, 863.51, 863.58, 864.73, 73/864.81, 23.31
See application file for complete search history.

(56) References Cited

U.S. PATENT DOCUMENTS

| | | | | |
|---|---|---|---|---|
| 3,771,960 A * | 11/1973 | Kim et al. | ............ | 436/152 |
| 3,965,749 A | 6/1976 | Hadden et al. | | |
| 4,898,190 A * | 2/1990 | Deal | ............ | 131/336 |
| 5,058,440 A | 10/1991 | Graze, Jr. | | |
| 5,083,422 A * | 1/1992 | Vogt | ............ | 60/782 |
| 5,106,240 A * | 4/1992 | Dirkse et al. | ............ | 406/138 |
| 5,220,795 A * | 6/1993 | Dodds et al. | ............ | 60/747 |
| 5,239,818 A * | 8/1993 | Stickles et al. | ............ | 60/804 |
| 5,410,907 A | 5/1995 | Strom et al. | | |
| 6,021,678 A | 2/2000 | Vardiman et al. | | |
| 6,260,359 B1 * | 7/2001 | Monty et al. | ............ | 60/752 |
| 6,481,299 B2 | 11/2002 | Silvis et al. | | |
| 7,044,009 B2 * | 5/2006 | Graze, Jr. | ............ | 73/863.03 |
| 2003/0205096 A1 | 11/2003 | Gehner et al. | | |
| 2003/0232449 A1 | 12/2003 | Mikkanen et al. | | |

FOREIGN PATENT DOCUMENTS

JP 57016333 1/1982
KR 366898 B 1/2003

* cited by examiner

*Primary Examiner*—Hezron Williams
*Assistant Examiner*—Nashmiya S. Fayyaz
(74) *Attorney, Agent, or Firm*—Finnegan, Henderson, Farabow, Garrett & Dunner

(57) ABSTRACT

A dilution tunnel having a flow chamber structure with an inlet, an outlet, and an internal flow passage for a sample gas, the sample gas being adapted to flow in a flow direction between the inlet and the outlet. The flow chamber structure having a plurality of pores that communicate between an outside region external of the flow chamber structure and the internal flow passage. The pores are adapted to introduce a diluting gas from the outside region into the internal flow passage. The flow chamber structure is adapted to provide a diluting rate of the dilution tunnel that varies in the flow direction of the dilution tunnel.

23 Claims, 4 Drawing Sheets

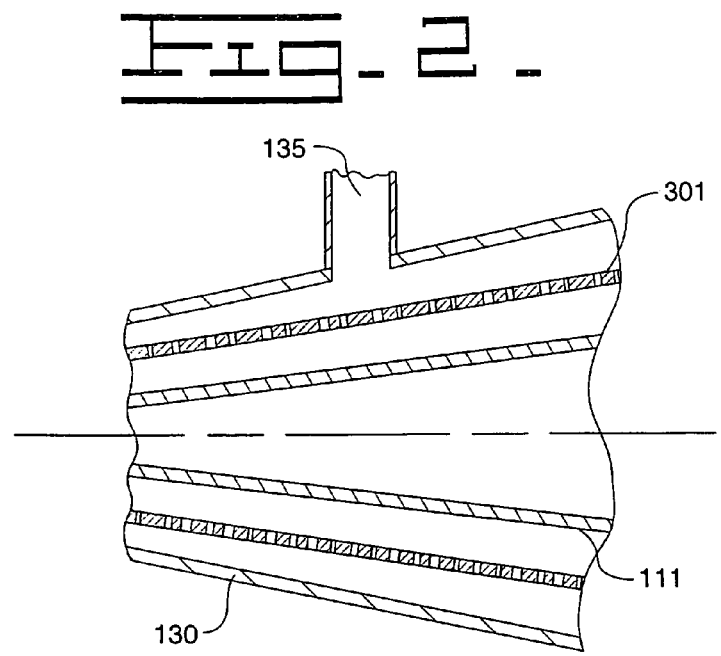
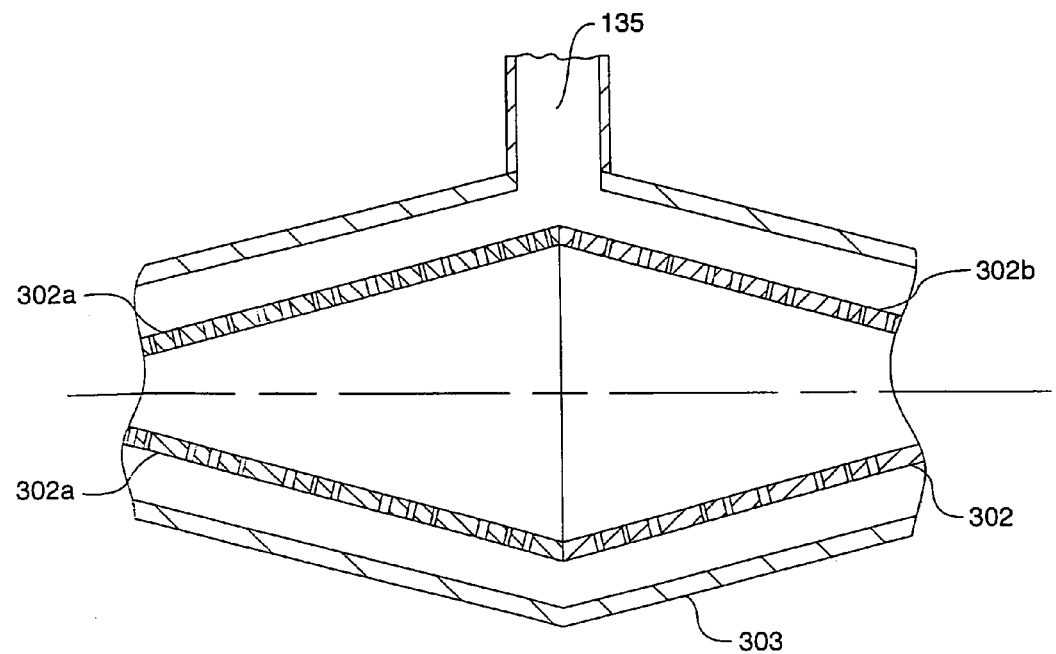

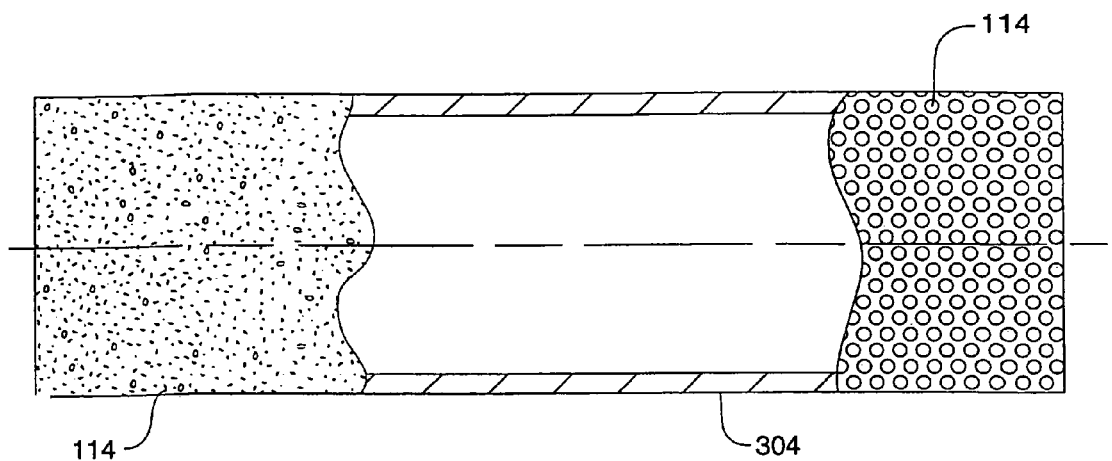
Fig_4_
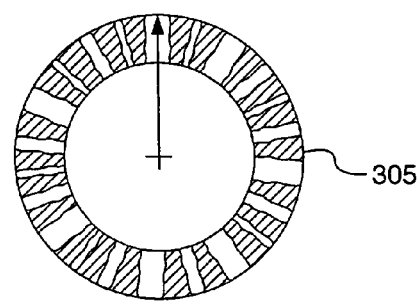
Fig_5_

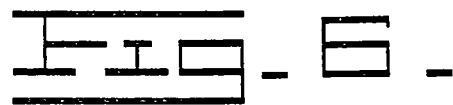
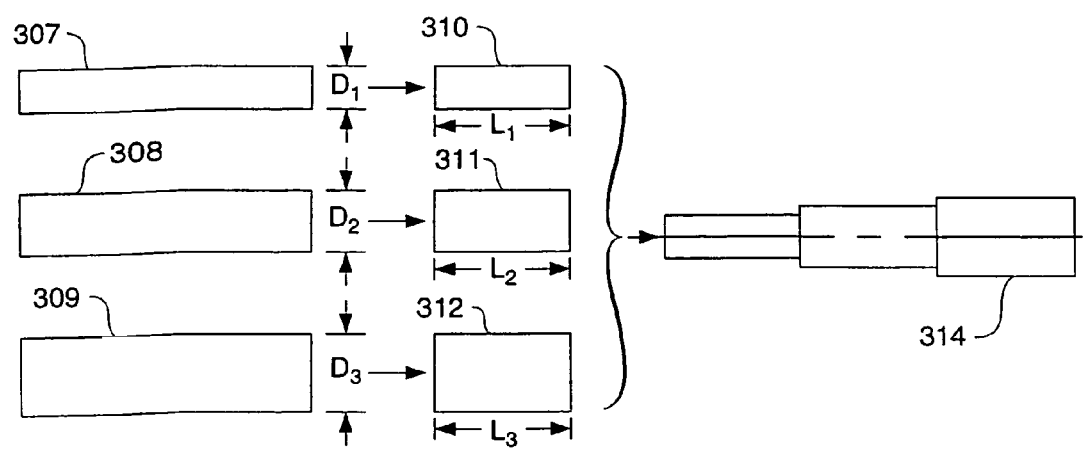
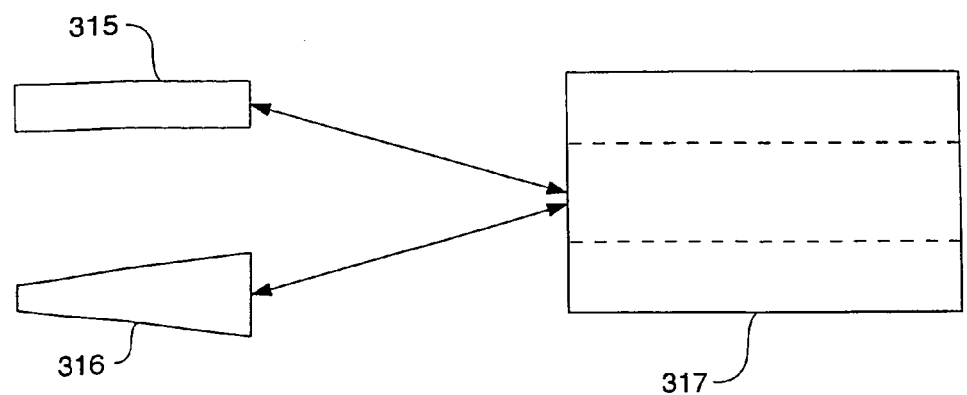

DILUTION TUNNEL

PRIORITY

This is a divisional of application Ser. No. 10/151,338, filed May 20, 2002, now U.S. Pat. No. 7,044,009 which is incorporated herein by reference.

TECHNICAL FIELD

This invention relates to a dilution tunnel for sampling gases, such as exhaust gases from engines or other effluent sources, and more particularly for sampling these gases to analyze particles contained therein.

BACKGROUND

With an increasing emphasis placed on protecting the environment, industries and governments are committing greater resources to monitoring and regulating existing stationary and non-stationary effluent sources as well as to developing new environmentally friendly stationary and non-stationary effluent sources.

For instance, exhaust gases or emissions from motorized vehicles are regulated by the U.S. Federal Government so as not to exceed certain maximum contaminant levels. Because of these regulations, increasingly more sophisticated testing equipment has been developed to test and analyze engines for conformance with such standards. As an example, regulations set by the U.S. Environmental Protection Agency (EPA) involve particulate limit standards for various types of engines such as diesel truck engines. The regulated particles are matter in the exhaust gas stream, other than condensed water, that can be collected after dilution. These particulates can include agglomerated carbon particles, absorbed hydrocarbons, and sulfates.

In order to comply with such regulations, industries involved in the manufacturing or use of effluent sources and government agencies responsible for enforcing such regulations have relied on systems that attempt to simulate the diluting process of the exhaust gases. Known methods include adding diluting air to the exhaust gas through a controlled sampling system that has a dilution tunnel. A significant challenge with these methods is the elimination of errors in measurements taken of the diluted exhaust gas and the diluting air streams and the need to precisely control their respective flow rates.

When the size of the effluent source, and more particularly, the mass flow of exhaust gas from the effluent source, permits, full sampling dilution systems may be used in which the total exhaust gas flow from the effluent source is mixed with a quantity of diluting air. However, when the size of the effluent source is so large that testing with a full sampling dilution system would not be practical due to the large size required for the corresponding dilution tunnel, proportional sampling dilution systems may be used in which only a portion of the exhaust gas flow is sampled, requiring a smaller dilution tunnel.

Investigations into the performance of dilution systems used today continue to indicate excessive variability between governmental agencies, testing laboratories, and effluent source manufacturers. This variability can have negative consequences. On the one hand, the discrepancies between the testing laboratories may translate into competitive advantages for the low-result testing laboratories. On the other hand, the observed test-to-test variability translates into increased test expenditure because a large number of tests are required to obtain statistically significant results. Although there are several particle mechanisms that influence test-to-test variability, those most significant are particle deposition on the dilution tunnel and tailpipe walls by thermophoresis, by mechanical processes such as diffusion, gravitational sedimentation and turbulence, and by reentrainment of deposited particles and hydrocarbon gas phase exchange of the soluble portion of the exhaust particles with the deposited wall bound particles. Therefore, elimination of the deposition mechanism is highly desirable.

U.S. Pat. No. 5,058,440 discloses a dilution tunnel aimed at reducing the variability of test results in part through the elimination of thermophoretic deposition of particles on the walls of the sampling device and corresponding hydrocarbon gaseous phase component exchange with these wall-bound particles; down-sizing the dilution tunnel to produce a fully portable sampling system that can yield results equivalent to those of large testing laboratories; and a sampling system that can monitor variable engine operating parameters, automatically control the rate of exhaust gas withdrawal and vary the air dilution rate within preselected guidelines within a normal range of operating temperatures and pressures.

In particular, U.S. Pat. No. 5,058,440 discloses a gas sampling system that uses a dilution tunnel, including a sampling probe disposed in an exhaust gas stream of an engine, a source of clean diluting air, and a filter assembly. The dilution tunnel includes an air distribution tube or diffuser tube having a plurality of distribution holes therethrough, a porous center tube having a plurality of micron-sized pores and defining a first chamber within the air distribution tube, and a housing forming a second chamber about the air distribution tube. The second chamber is connected to a diluting air source, and the center tube is connected between a sampling probe in the exhaust gas flow and a filter assembly.

The known gas sampling systems, however, lack the ability to change the rate of dilution of a sample flow of gas, so that these systems do not allow accurate simulations to be made of a variety of diluting processes. To appreciate the extent of this shortcoming, it is important to understand that accurate attainment of particle analysis, such as representative particle size measurement results, depends strongly on simulations of atmospheric diluting processes as qualified for a given application.

For example, exhaust gas from the exhaust pipe of a large diesel truck hauling a trailer may experience the following particular diluting process characterized by a series of different diluting rates at various distances from the exhaust pipe: (1) a fast diluting rate near the exhaust pipe where the gas is initially introduced into the atmosphere, (2) a slow diluting rate over the trailer portion where the air flow is relatively stable or laminar, and (3) an intermediate diluting rate behind the trailer where the air flow is turbulent. On the other hand, in a stationary effluent source, such as a power plant, the exhaust gas may experience a different diluting process determined primarily as a function of time out of the exhaust pipe or stack and distance from the exhaust stack.

Therefore, there is a need for introducing additional degrees of freedom into gas sampling systems that use dilution tunnels, so that the sample gas can be diluted in a controlled manner that better simulates the actual diluting process for a given application.

The present invention is directed to overcoming one or more of the problems as set forth above.

SUMMARY OF THE INVENTION

It is, therefore, desirable to provide a dilution tunnel that adds additional degrees of freedom to permit more accurate diluting simulations to be carried out in a cost-effective manner.

In one aspect of the invention, a dilution tunnel is provided having a flow chamber structure with an inlet, an outlet, and an internal flow passage for a sample gas, the sample gas being adapted to flow in a flow direction between the inlet and the outlet. The flow chamber structure having a plurality of pores that communicate between an outside region external of the flow chamber structure and the internal flow passage. The pores are adapted to introduce a diluting gas from the outside region into the internal flow passage. The flow chamber structure is adapted to provide a diluting rate of the dilution tunnel that varies in the flow direction of the dilution tunnel.

According to another aspect of the invention, a dilution tunnel is provided having a porous tube with an inlet and an outlet and a flow axis passing through the porous tube, the inlet, and the outlet; wherein the porous tube defines an internal flow passage for a sample gas between the inlet and the outlet, and the flow axis defines an axial flow direction of the sample gas through the internal flow passage. The porous tube has a plurality of pores that communicate between an outside region external of the porous tube and the internal flow passage, with the pores being adapted to introduce a diluting gas into the internal flow passage; and wherein a geometry of the dilution tunnel varies in the axial flow direction.

According to another aspect of the invention, the porosity of the porous tube varies in at least one of the axial flow direction and a radial direction that extends radially outward from the flow axis.

According to yet another aspect of the present invention, a gas sampling system for analyzing a first gas is provided having a dilution tunnel and a second gas source. The dilution tunnel includes a porous tube having an inlet and an outlet and a flow axis passing through the porous tube, the inlet, and the outlet. The porous tube defines an internal flow passage for the first gas between the inlet and the outlet, and the flow axis defines an axial flow direction of the first gas through the porous tube. The porous tube has a plurality of pores that communicate an outside region external of the porous tube and the internal flow passage, with the pores being adapted to introduce the second gas into the internal flow passage. A geometry of the dilution tunnel varies in the axial flow direction.

According to still another aspect of the invention, a porosity of the porous tube in the gas sampling system varies in at least one of the axial flow direction and a radial direction that extends radially outward from the flow axis.

In accordance with another aspect of the invention, a method of diluting a first gas with a second gas is performed, including the steps of passing a first gas through a first region in a flow direction along a flow axis of the first region; passing a second gas through a second region, the first and second regions being separated by a porous structure; and introducing the second gas into the first region at a variable rate, determined by the porous structure, that changes in the flow direction of the first gas.

In accordance with yet another aspect of the present invention, the dilution tunnel is manufactured by providing a plurality of porous tubes, each porous tube having a different diluting rate defined by at least one of the porous tube's geometry and porosity; cutting respective sections from each porous tube; and serially coupling the respective sections to each other to form an single porous tube that defines an internal flow passage.

BRIEF DESCRIPTION OF THE DRAWINGS

The above-mentioned and other features and advantages of this invention are described below with reference to the accompanying drawings, wherein:

FIG. 2 is schematic and partial cross-sectional view of a dilution tunnel in accordance with the first embodiment of the present invention;

FIG. 3 is schematic and partial cross-sectional view of a dilution tunnel in accordance with the first embodiment of the present invention;

FIG. 4 is schematic and partial cross-sectional view of a dilution tunnel in accordance with a second embodiment of the present invention;

FIG. 5 cross-sectional view of a porous tube in accordance with the second embodiment of the present invention;

FIG. 6. is schematic view of a method of manufacturing a dilution tunnel in accordance with a third embodiment of the present invention.

FIG. 7. is schematic view of dilution tunnels in accordance with a fourth embodiment of the present invention.

DETAILED DESCRIPTION

Figure 1:
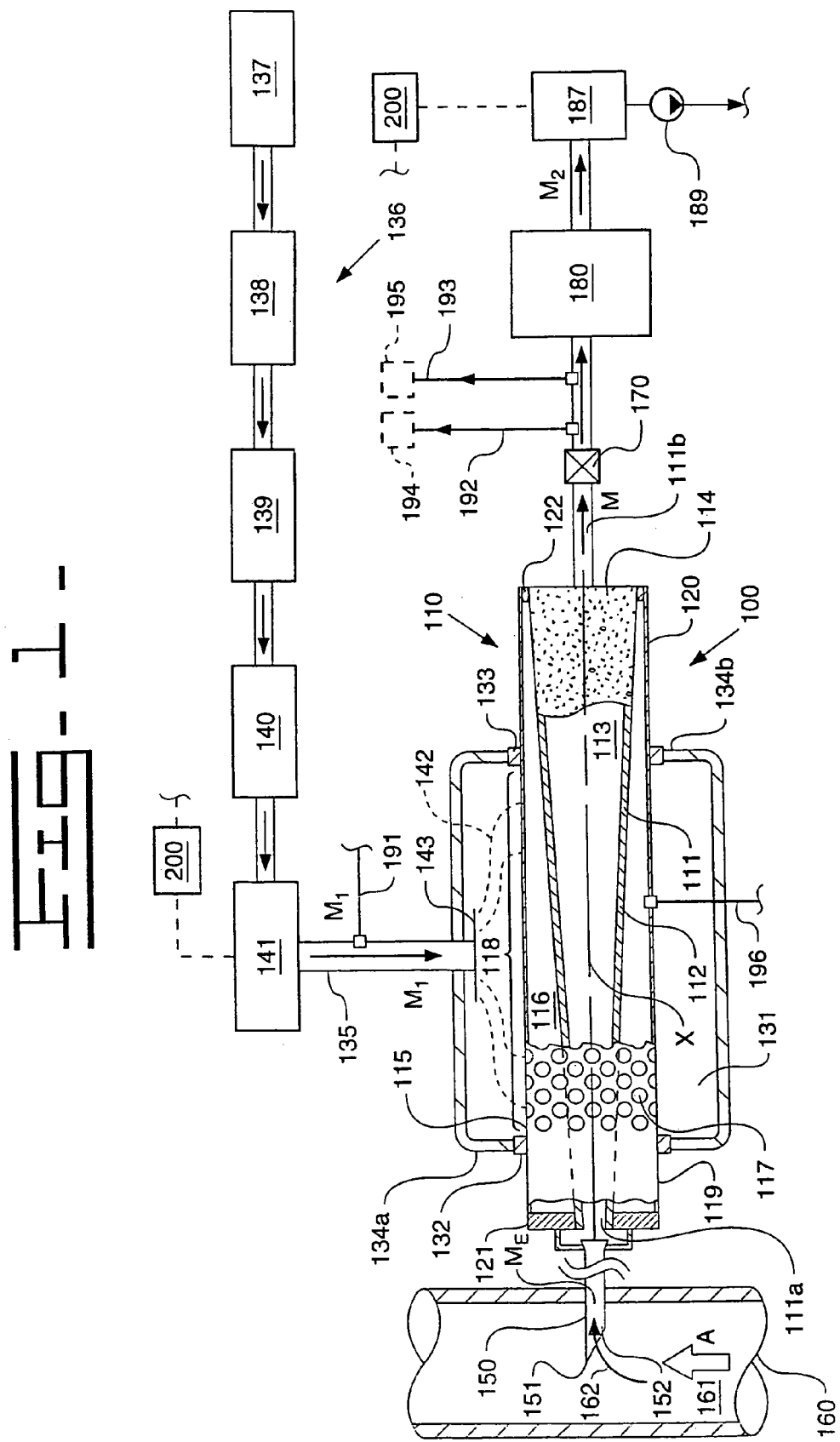
FIG. 1 is a schematic and partial cross-sectional view of a gas sampling system having a dilution tunnel in accordance with a first embodiment of the present invention.

While the invention is open to various modifications and alternative forms, specific embodiments thereof are shown by way of examples in the drawings and are described herein in detail. There is no intent to limit the invention to the particular forms disclosed.

The invention relates to a dilution tunnel for use in a gas sampling system to analyze particles in a sample gas, for example, taken from an engine exhaust. The dilution tunnel is configured-to dilute the sample gas by introducing a diluting gas, such as clean air, into the sample gas. To carry out this diluting process, the dilution tunnel includes a porous tube that allows the sample gas and diluting gas to mix in a controlled manner. The diluted sample gas can then be analyzed to determine such characteristics as the amount and nature of the particles in the gas. The diluting process can be used in numerous applications, including, without limitation, the simulation of exhaust gases in the atmosphere from stationary or non-stationary sources. As discussed in greater detail below, additional degrees of freedom can be introduced into the diluting process by using dilution tunnels having varying geometry and/or porosity that provide varying rates of sample gas dilution along the flow path of the sample gas. These additional degrees of freedom permit more accurate diluting simulations to be carried out in a cost-effective manner.

As shown in FIGS. 1 and 2, a gas sampling system 100 constructed in accordance with the present invention includes a dilution tunnel 110 having a flow chamber structure that defines an internal flow passage for an exhaust gas to pass in a flow direction between an inlet and an outlet of the flow chamber. As illustrated in FIG. 1, the flow chamber structure can be an elongated porous structure or tube 111 extending between an inlet 111a and an outlet 111b of the porous tube and having a flow axis X passing through the porous tube, the inlet and the outlet. The porous tube 111 has a wall (or plurality of walls) 112 that defines an internal flow passage 113 for the flow of a sample gas between the inlet 111*a* and the outlet 111*b*. The flow axis X defines an axial flow direction of the sample gas through the internal flow passage 113. Pores 114 (for example, but not limited to, 0.5 micron in diameter) are formed in the wall 112 and communicate an outside region 116 external of the porous tube 111 with the internal flow passage 113 to introduce a gas into the internal flow passage. The porous tube 111 may be made from sintered stainless steel having a plurality of pores 114 that provide the desired precisely controlled porosity.

The dilution tunnel 110 may include a diffuser tube 115 formed around the porous tube 111, so as to define a first annular chamber (outside region) 116 peripherally about the porous tube 111. The diffuser tube 115 is preferably an elongated tube of stainless steel or the like that has a plurality of distribution holes 117 radially therethrough in a central region 118 of the dilution tunnel 110, and opposite end portions 119 and 120 without such holes. The distribution holes 117 are sized and arranged as desired to promote the desired flow distribution around the porous tube 111.

When the dilution tunnel includes the diffuser tube 115, the porous tube 111 may extend the length of the diffuser tube 115. In this case, a pair of diffuser tube sealing rings 121 and 122 are secured to the diffuser tube 115 and the porous tube 111 at the opposite ends thereof.

The dilution tunnel 110 also includes a housing 130 that forms a second annular chamber 131 peripherally about the central region 118 of the diffuser tube 115. A pair of housing sealing rings 132 and 133 securely connect respective collars 134*a* and 134*b* of the housing to the diffuser tube 115 intermediate the central region 118 and the end portions 119 and 120. An inlet port 135 is formed radially through the housing 130 and is in communication with a controlled flow rate source of a diluting gas (e.g., clean air 142) and indicated generally by the reference number 136. Preferably, the diluting gas source 136 includes, in serially arranged order, a pressurized diluting air reservoir 137, a filter 138, a scrubber 139 to remove oil and/or hydrocarbons, a desiccant filter or drying unit 140 to remove excess moisture, a first mass flow controller 141 that is preferably adjustable, and any other devices or plumbing necessary to introduce the clean air 142 into the housing 130 to carry out the diluting process. For example, a diffuser screen 143 may be located near the inlet 135 to improve the flow of clean air around the porous tube 111 or diffuser tube 115 and, thus, reduce the residence time for molecules of air in the dilution chamber to a desired level.

When the diffuser tube 115 is not included, the porous tube 111 may extend the length of the housing 130 and the pair of housing sealing rings 132 and 133 may securely interconnect the respective collars 134*a* and 134*b* of the housing directly to the porous tube 111.

The porous tube 111 is connected to a sampling probe 150 by any conventional coupling or plumbing not shown. The sample probe 150 can then extend into an exhaust pipe 160 of an effluent source. The probe 150 has a nose portion 151 defining an inlet passage 152 facing an upstream direction of the exhaust gas flow 161 relative to the arrow A. Thus, a proportionate sample of a particle-laden exhaust gas flow 161, as indicated by the reference numeral 162, is directed to the interior of the inlet end of the porous tube 111 near the ring 121. When the gas sampling system analyzes the proportional sample of the exhaust gas flow 161, the system can be characterized as a proportional sampling diluting gas system. Alternatively, a full sampling diluting gas system may be used in which the probe 150 is sized to capture the total exhaust gas flow 161 and the system dilutes the captured flow with a quantity of diluting gas.

The opposite or outlet end of the porous tube 111, at the ring 122, is connected to a shut-off valve 170 and filter 180. The filter 180 may be a gravimetric filter to perform particle sampling. Other particle analyzing devices that perform particle measurement (e.g., such as a particle size measurement devices or real-time particle measurement devices as two non-limiting examples, may be used in place of or in conjunction with the gravimetric filter 180. Such particle measurement devices can include particle scanners (e.g., a scanning mobility particle size scanner, SMPS; or an electrostatic low pressure impactor, ELPI).

The outlet of the filter 180 is in serial communication with a second mass flow controller 187 that is preferably adjustable. A suction pump 189 is serially connected to the outlet of the second mass flow controller 187.

Sample branches 191-193 may be included in the gas sampling system 100 as needed. For example, branch 191 may be provided prior to the inlet port 135 to test the quality of a sample $m_1$ of the air. Also branches 192 and 193 may be provided between the outlet of the diluting tunnel and the input of the gravimetric filter to take measurements with respective particle scanners 194 and 195 on a percentage of the gas flow $m_2$, $m_3$.

Additionally, sensors, such as temperature sensors 196 may be placed along the flow path of the sample of exhaust gas to confirm that the diluting process is being carried out at the appropriate temperature, or to confirm other physical parameters. Such monitoring can provide important feedback to ensure that the desired control process is being exerted on the system.

To the extent required, the first and second mass flow controllers 141 and 187 may be sophisticated electrically controlled mass flow controllers. The second mass flow controller 187 may be a total flow rate controlling instrument, and the first mass flow controller 141 may be an electrically controlled, slave mass flow controller for precisely controlling the diluting gas flow into the housing 130. In this case, first and second mass flow controllers 141 and 187 may be electrically connected to a microprocessor 200. Accordingly, measurements of the particles in the exhaust gas can be determined by the microprocessor by subtracting from the sum of the mass flow $M_1$ of clean air through the first mass flow controller 141 and the mass flow $M_E$ of the proportionate sample of exhaust gas through the probe 150 (i.e., $M_1 + M_E$) the sum of the mass flow $M_2$ through the second mass flow controller 187 and any mass flow through the branches $m_1$, $m_2$, $m_3$ plus any remaining mass flow out of the system, E (i.e., $M_2 + m_1 + m_2 + m_3 + E$).

According to a first embodiment of the invention shown in FIG. 1, the porous tube 111 of the dilution tunnel 110 is in the form of a cone about the flow axis X so that the diluting rate varies axially along the flow of the sample exhaust gas 162 as a function of the geometry of the porous tube, in this case, the cross-sectional area of the porous tube 111 taken in a direction orthogonal to the flow axis X. The cross-sectional area of the porous tube 111 taken in a direction orthogonal to the axis X includes the sum of the cross-sectional areas of the internal flow passage and the wall thickness of the porous tube.

As the conical porous tube 111 expands, the external area of the porous tube (or porous tube surface area) increases, as does the cross-sectional area of the internal passage 113, thereby increasing the diluting rate. As also shown in FIG. 1, the diffuser tube 115, if included, may have a constant cross-sectional area axially along the flow of the sample exhaust gas 162. Similarly, the housing 130 may have a constant cross-sectional area axially along the flow of the sample exhaust gas 162.

On the other hand, as shown in FIG. 2, a diffuser tube 301 may be used that is also in the form of a cone and concentric with the porous tube 111, such that the diffuser tube expands in the axial flow direction. Accordingly, the diffuser tube would have a cross-sectional area that varies axially along the flow of the sample exhaust gas 162. Similarly, a housing 130 may be used that is in the form of a cone and concentric with the porous tube 111, such that the housing expands in the axial flow direction. Accordingly, the housing would also have a cross-sectional area that varies axially along the flow of the sample exhaust gas 162. Accordingly, a constant ratio of diluting air volume to porous tube surface area can be maintained axially along the flow of the sample exhaust gas 162.

As shown in FIG. 3, a porous tube 302 in the form of two cones may be used, a first cone 302a expanding in the direction of flow of the sample exhaust gas 162 until it meets a second cone 302b contracting in the direction of flow of the sample exhaust gas 162. Accordingly, the cross-sectional area of the internal flow passage of the porous tube increases and then decreases in the axial flow direction. Again, a housing 303 having a corresponding form may be used in combination with the porous tube 302. Also, while not shown, a diffusing tube have a corresponding form may be added.

While the foregoing examples represent certain preferred geometric configurations for the dilution tunnel, they are not intended to be an exhaustive list of all the possible geometric configurations contemplated by the invention. Clearly, there remain numerous other possible configurations. For example, a porous tube in the form of a cone expanding in the direction of exhaust gas flow can be combine with a diffuser tube and housing in the shape of a cone contracting in the direction of exhaust gas flow. Still, the porous tube, the diffuser tube, and the housing may take on any other geometric configurations that permit variations in the diluting rate in the direction of exhaust gas flow, or that maintain a constant diluting rate under the given flow conditions. On the other hand, a porous tube with a uniform cross-sectional area in the direction of the exhaust gas flow may be used in combination with a housing or diffuser tube in the form of a cone or other geometric configuration.

However, a common feature in this first embodiment of the invention is a variation in the geometry of the dilution tunnel, and preferably a variation in the cross-sectional area of part or all of the dilution tunnel, including one or more of the porous tube, the diffuser tube, and the housing, taken in a direction substantially orthogonal to the flow of exhaust gas. This variation in cross-sectional area provides added degrees of freedom that advance the capabilities for sampling a gas using a dilution tunnel.

According to a second embodiment of the invention as shown in FIG. 4, the cross-sectional area of the porous tube 304 may be constant in the axially direction along the flow of the sample exhaust gas 162, while the porosity, such as the size of the pores 114 or density of the pores 114 (i.e., the number of pores per unit area or volume), varies in that direction. For example, to carry out the diluting process at a varying rates, the size of the pores 114 at the beginning of the flow of the sample exhaust gas 162 can be in the order of 0.5 microns and increase in size to the order of 4 to 5 microns at the end of the flow. The variation in pore size can be linear or non-linear as required to carry out the desired dilution process.

Additionally, the porosity can vary in the radial direction of the porous tube that extends radially outward from the flow axis. For example, as illustrated in FIG. 5, a porous tube 305 may be formed from sintered stainless steel that has been compressed by different amounts in the radial direction so that the size of the pores decrease in a direction radially outward from the center of the porous tube 305. Alternatively, this variation in porosity may be achieve by forming a porous tube from different layers of porous material, each layer having pores of a different size.

Furthermore, while not shown, the density of the pores can vary in the axial direction along the flow of the sample exhaust gas 162 or in the radial direction of the porous tube.

While the foregoing variations in porosity represent certain preferred configurations for the dilution tunnel, they are not intended to be an exhaustive list of all such possible configurations contemplated by the invention. However, a common feature in this second embodiment is that the porosity of the porous tube varies in the axial direction along the flow of the sample exhaust gas 162, in the radial direction of the porous tube 111, or both. This variation in porosity also provides added degrees of freedom that advance the capabilities for sampling a gas using a dilution tunnel.

While the foregoing two embodiments have been described separately, the present invention also contemplates combining these embodiments, thereby further adding to the degrees of freedom for carry out the diluting process. For example, a porous tube can be used that has the form of a cone and has pores that increases in size from the smaller end of the porous tube to the larger end thereof. Such a porous tube could dramatically increase the diluting rate in the expansion direction of the porous tube.

Therefore, variations in the geometry of the dilution tunnel and/or porosity of the porous tube can be made so that the diluting rate of the dilution tunnel varies in an axial direction of the dilution tunnel.

According to a third embodiment of the invention as shown in FIG. 6, the dilution tunnel can be manufactured using short porous tube sections of various diameters, porosity, or a combination thereof, and welding these sections together in axial communication to create the desired overall form. For example, as shown in FIG. 6, a first porous tube section 310 have a first diameter $D_1$ can be cut from a supply of tube stock 307 to a length $L_1$. Similarly, second and third porous tube sections 311 and 312 having respective second and third diameters $D_2$ and $D_3$ can be cut from different tube stocks 308, 309 to respective lengths $L_2$ and $L_3$. Each porous tube stock 307-309 can have a different diluting rate defined its geometry and/or porosity. Subsequently, each of the porous tube sections can be serially coupled to form a single porous tube 314 in the shape of, for example, a cone, that defines a internal flow passage. The sections can be coupled directly together by welding, or they can be coupled using any other manner and can include intermediary portions between each section.

With this sectioning manufacturing process, therefore, standard porous tube sections with respective uniform cross-sections and uniform pore sizes may be used to form a porous tube having a variable cross-section, thereby reducing the manufacturing cost. Also contemplated by the invention is the manufacture of the diffuser tube and housing using this sectioning manufacturing process.

According to a fourth embodiment of the invention, the gas sampling system 100 may be provided with a plurality of dilution tunnels, each dilution tunnel being an interchangeable cartridge having a different diluting rate and configured to be removably disposed in the gas sampling system. As shown in FIG. 7, this feature can be achieved by using porous tube cartridges 315 and 316, for example, which are configured to be removably inserted into the housing 317, which, in turn, is configured to receive these cartridges. Alternatively, the cartridges may include the porous tube and the diffuser tube or the porous tube, the diffuser tube and the housing. The advantage of using cartridges is that different predetermined diluting processes can be carried out by merely replacing the cartridge and instructing the microprocessor as required.

INDUSTRIAL APPLICABILITY

The dilution tunnel of the invention provides several advantages over the conventional dilution tunnel having uniform geometry and porosity. In particular, the dilution tunnel of the invention provides added degrees of freedom in carrying out the diluting process.

For example, in the case of a non-stationary effluent source, such as a moving truck hauling a trailer, the diluting rates typically change from fast to slow to intermediate. These diluting rates can be accurately simulated in a laboratory or on-site using a gas sampling system having a dilution tunnel in accordance with the invention with varying geometry and/or porosity that dilutes a sample exhaust gas from the truck at corresponding varying rates.

Such accurate simulations can then be used in the research and development of truck engines to ensure that new designs for these engines meet or exceed standards set by EPA regulations. Alternatively, the simulations can be used to establish whether trucks currently in use are meeting these standards.

In the case of a stationary effluent source, such as a power plant, the diluting rates of the exhaust gas change as a function of time out of the stack and distance from the exhaust stack. These diluting rates can be accurately simulated on-site using a gas sampling system having a dilution tunnel in accordance with the invention with varying geometry and/or porosity that dilutes a sample exhaust gas from the stack at similar corresponding varying rates.

Therefore, an advantageous effect of the present invention is the provision of a dilution tunnel that provides added degrees of freedom for carrying out different diluting processes in an accurate and cost-effective manner.

In view of the foregoing, it is readily apparent that the subject dilution tunnel provides an improved mechanism for diluting a first gas with a second gas.

Other aspects, objects and advantages of the present invention can be obtained from a study of the drawings, the disclosure and the appended claims.

The invention claimed is:

1. A dilution tunnel, comprising:
a porous tube having an inlet fluidly coupled to an exhaust gas producing source, an outlet, and a flow axis passing through said porous tube, the inlet, and the outlet, said porous tube defining an internal flow passage for exhaust gas between the inlet and the outlet, the flow axis defining an axial flow direction of the exhaust gas through said porous tube, and the internal flow passage being substantially symmetrical about the flow axis;
said porous tube including a porous section having a plurality of open pores formed in a wall of the porous tube that communicate between an outside region external of said porous tube and the internal flow passage, said pores being adapted to introduce a diluting gas from the outside region into the internal flow passage; and
wherein a porosity of said porous section varies in at least one of the axial flow direction and around a periphery of the porous tube.

2. The dilution tunnel according to claim 1, wherein a size of said pores varies in the axial flow direction.

3. The dilution tunnel according to claim 1, wherein a size of said pores varies around the periphery of the porous tube.

4. The dilution tunnel according to claim 1, wherein a density of said pores varies in at least one of the axial flow direction and around the periphery of the porous tube.

5. The dilution tunnel according to claim 1, wherein a cross-sectional area of said porous tube taken in a direction orthogonal to the flow axis varies in the axial flow direction.

6. The dilution tunnel according to claim 2, wherein said porous tube is formed from a plurality of sections of porous tubes, wherein the size of said pores in each section are substantially the same.

7. The dilution tunnel according to claim 3, wherein said porous tube is formed from sintered steel that has been compressed by different amounts in the radial direction so that the size of said pores varies around the periphery of the porous tube.

8. A gas sampling system for analyzing exhaust gas produced by an exhaust gas producing source, comprising:
a dilution tunnel fluidly coupled to the exhaust gas producing source; and
a gas source that supplies a diluting gas;.
wherein said dilution tunnel includes a porous tube having an inlet and an outlet and a flow axis passing through said porous tube, the inlet, and the outlet; said porous tube defining an internal flow passage for exhaust gas between the inlet and the outlet, the flow axis defining an axial flow direction of the exhaust gas through said porous tube; and the internal flow passage being substantially symmetrical about the flow axis; said porous tube including a porous section having a plurality of open pores formed in a wall of the porous tube that communicate between an outside region external of said porous tube and the internal flow passage, said pores being adapted to introduce said diluting gas into the internal flow passage; and
wherein a porosity of said porous section varies in at least one of the axial flow direction and around a periphery of the porous tube.

9. The gas sampling system according to claim 8, wherein a size of said pores varies in the axial flow direction.

10. The gas sampling system according to claim 8, wherein a size of said pores varies around the periphery of the porous tube.

11. The gas sampling system according to claim 8, wherein a cross-sectional area of said porous tube taken in a direction orthogonal to the flow axis varies in axial flow direction.

12. The gas sampling system according to claim 8, wherein said dilution tunnel is one of a plurality of interchangeable cartridges for said gas sampling system, wherein each cartridge has a different diluting rate.

13. The gas sampling system according to claim 8, wherein said gas source is a clean air source that supplies clean air to said dilution tunnel; and
wherein said gas sampling system further includes a sampling probe upstream of said dilution tunnel and at least one of a gravimetric filter and a particle scanner downstream of the dilution tunnel;
a first mass flow controller between said clean air source and said dilution tunnel; and
a second mass flow controller downstream of said at least one of said gravimetric filter and said particle scanner.

14. A dilution tunnel, comprising:
a porous tube having an inlet fluidly coupled to an exhaust gas sampling probe, an outlet, and a flow axis passing through said porous tube, the inlet, and the outlet, said porous tube defining an internal flow passage for exhaust gas between the inlet and the outlet, the flow axis defining an axial flow direction of exhaust gas through said porous tube, and the internal flow passage being substantially symmetrical about the flow axis;

said porous tube having a plurality of pores that communicate between an outside region external of said porous tube and the internal flow passage, said pores being adapted to introduce a diluting gas from the outside region into the internal flow passage;

wherein a size of said pores varies in at least one of the axial flow direction and around a periphery of the porous tube.

15. The dilution tunnel according to claim 14, wherein a density of said pores varies in at least one of the axial flow direction and around the periphery of the porous tube.

16. The dilution tunnel according to claim 14, wherein a cross-sectional area of said porous tube taken in a direction orthogonal to the flow axis varies in the axial flow direction.

17. The dilution tunnel according to claim 14, wherein said porous tube is formed from sintered steel that has been compressed by different amounts in the radial direction so that the size of said pores varies around the periphery of the porous tube.

18. A gas sampling system for analyzing a first gas, comprising:
a dilution tunnel; and
a second gas source that supplies a second gas;
wherein said dilution tunnel includes a porous tube having an inlet, an outlet fluidly coupled to a particle analyzing system, and a flow axis passing through said porous tube, the inlet, and the outlet;
said porous tube defining an internal flow passage for said first gas between the inlet and the outlet, the flow axis defining an axial flow direction of said first gas through said porous tube, and the internal flow passage being substantially symmetrical about the flow axis;
said porous tube having a plurality of pores that communicate between an outside region external of said porous tube and the internal flow passage, said pores being adapted to introduce said second gas into the internal flow passage; and
wherein a size of said pores varies in at least one of the axial flow direction and around a periphery of the porous tube.

19. The gas sampling system according to claim 18, wherein a density of said pores varies in at least one of the axial flow direction and around the periphery of the porous tube.

20. The gas sampling system according to claim 18, wherein a cross-sectional area of said porous tube taken in a direction orthogonal to the flow axis varies in the axial flow direction.

21. A dilution tunnel, comprising:
a porous tube including
an inlet end configured to receive exhaust gas from an exhaust gas producing source,
an outlet end in fluid communication with a particle analyzing system,
an internal flow passage for the exhaust gas between the inlet and the outlet, and
a porous section having a plurality of pores that communicate between a region external of the porous tube and the internal flow passage, the plurality of pores being configured to introduce a diluting gas from the region external of the porous tube into the internal flow passage,
wherein a porosity of the porous section varies in at least one of an axial direction and around a periphery of the porous tube, and the pore sizes of the plurality of pores are less than or equal to 5 microns.

22. The dilution tunnel of claim 21, wherein the pore sizes are greater than or equal to 0.5 microns.

23. The dilution tunnel of claim 21, wherein the pore size of at least one pore of the plurality of pores varies along a longitudinal axis of the at least one pore.

* * * * *